United States Patent
Richter et al.

(10) Patent No.: US 9,327,120 B2
(45) Date of Patent: May 3, 2016

(54) SYSTEM AND METHOD FOR ANIMAL-HUMAN NEURAL INTERFACE

(71) Applicant: NORTHWESTERN UNIVERSITY, Evanston, IL (US)

(72) Inventors: Claus-Peter Richter, Skokie, IL (US); Petrina LaFaire, Chicago, IL (US); Xiaodong Tan, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/477,403

(22) Filed: Sep. 4, 2014

(65) Prior Publication Data

US 2015/0066107 A1    Mar. 5, 2015

Related U.S. Application Data

(60) Provisional application No. 61/873,720, filed on Sep. 4, 2013.

(51) Int. Cl.
*A61N 1/36* (2006.01)
*A61N 1/05* (2006.01)

(52) U.S. Cl.
CPC .......... *A61N 1/36032* (2013.01); *A61N 1/0541* (2013.01)

(58) Field of Classification Search
CPC ................ A61N 1/0541; A61N 1/36032
See application file for complete search history.

(56) References Cited

U.S. PATENT DOCUMENTS 7,991,475 B1 *   8/2011   Tang ................. A61B 5/04001
                                                    600/373
2009/0125081 A1   5/2009   Spitzer et al.
(Continued)

FOREIGN PATENT DOCUMENTS

WO        03/063543 A2   7/2003
WO    2013/009805 A1   1/2013

OTHER PUBLICATIONS

Berenstein, C.K., Mens, L.H., Mulder, J.J., Vanpoucke, F.J. 2008. Current steering and current focusing in cochlear implants: comparison of monopolar, tripolar, and virtual channel electrode configurations. Ear and hearing 29, 250-60.
(Continued)

*Primary Examiner* — Eric D. Bertram
(74) *Attorney, Agent, or Firm* — Locke Lord LLP; Tim Tingkang Xia, Esq.

(57) ABSTRACT

Aspects of the invention include system and method for transmitting neural data extracted from an electrical signal of a non-human mammal to a human. The system includes an electrode implantable into the animal auditory nerve, brainstem, or midbrain of the non-human mammal, configured to record the electrical signal of the non-human mammal, the electrical signal being in the form of sequences of pulses or pulse trains encoding frequency information of the non-human mammal, a processing device electrically coupled with the electrode, configured to process the electrical signal and convert the processed electrical signal into a digital signal, a transmitting device electrically coupled with the processing device, configured to transmit the digital signal, and a receiving device electrically coupled with the transmitting device, configured to receive the transmitted digital signal, convert the received digital signal into a sensory output perceptible to the human, and apply the sensory output to the human.

20 Claims, 6 Drawing Sheets

(56) References Cited

U.S. PATENT DOCUMENTS

2011/0307079 A1    12/2011  Oweiss et al.
2012/0029377 A1    2/2012  Polak

OTHER PUBLICATIONS

Choi, C.T., Hsu, C.H. 2009. Conditions for generating virtual channels in cochlear prosthesis systems. Annals of biomedical engineering 37, 614-24.
Koch, D.B., Downing, M., Osberger, M.J., Litvak, L. 2007. Using current steering to increase spectral resolution in CII and HiRes 90K users. Ear and hearing 28, 38S-41S.
Landsberger, D.M., Srinivasan, A.G. 2009. Virtual channel discrimination is improved by current focusing in cochlear implant recipients. Hearing research 254, 34-41.
Mens, L.H., Berenstein, C.K. 2005. Speech perception with mono- and quadrupolar electrode configurations: a crossover study. Otol Neurotol 26, 957-64.
Middlebrooks, J.C., Bierer, J.A. 2002. Auditory cortical images of cochlear-implant stimuli: coding of stimulus channel and current level. J Neurophysiol 87, 493-507.
Middlebrooks, J.C., Snyder, R.L. 2010. Selective electrical stimulation of the auditory nerve activates a pathway specialized for high temporal acuity. J Neurosci 30, 1937-46.
Moreno, Le., Rajguru, S.M., Matic, A.I., Yerram, N., Robinson, A.M., Hwang, M., Stock, S., Richter, C.-P. 2011. Infrared neural stimulation: beam path in the guinea pig cochlea. Hearing research PMID: 21763410.
Ohlemiller, K.K., Echteler, S.M. 1990. Functional correlates of characteristic frequency in single cochlear nerve fibers of the Mongolian gerbil. J Comp Physiol A 167, 329-38.
Ohlemiller, K.K., Siegel, J.H. 1998. Temporal aspects of the effects of cooling on responses of single auditory nerve fibers. Hearing research 123, 78-86.
Ohlemiller, K.K., Echteler, S.M., Siegel, J.H. 1991. Factors that influence rate-versus-intensity relations in single cochlear nerve fibers of the gerbil. J Acoust Soc Am 90, 274-87.
Richter, C.-P., Rajguru, S.M., Matic, A.I., Moreno, E.L., Fishman, A.J., Robinson, A.M., Suh, E., Walsh Jr., J.T. 2011. Spread of cochlear excitation during stimulation with optical radiation: Inferior colliculus measurements. Journal of neural engineering 8, 056006.
Richter, C.P., Matic, A.I., Wells, J.D., Jansen, E.D., Walsh, J.T., Jr. 2011. Neural stimulation with optical radiation. Laser Photon Rev 5, 68-80.
Sharma, V., McCreery, D.B., Han, M., Pikov, V. 2010. Bidirectional telemetry controller for neuroprosthetic devices. IEEE transactions on neural systems and rehabilitation engineering: a publication of the IEEE Engineering in Medicine and Biology Society 18, 67-74.
Shepherd, R.K., Baxi, J.H., Hardie, N.A. 1999. Response of inferior colliculus neurons to electrical stimulation of the auditory nerve in neonatally deafened cats. J Neurophysiol 82, 1363-80.
Shepherd, R.K., Linahan, N., Xu, J., Clark, G.M., Araki, S. 1999. Chronic electrical stimulation of the auditory nerve using non-charge-balanced stimuli. Acta oto-laryngologica 119, 674-84.
Snyder, R.L., Bierer, J.A., Middlebrooks, J.C. 2004. Topographic spread of inferior colliculus activation in response to acoustic and intracochlear electric stimulation. J Assoc Res Otolaryngol 5, 305-22.
Snyder, R.L., Middlebrooks, J.C., Bonham, B.H. 2008. Cochlear implant electrode configuration effects on activation threshold and tonotopic selectivity. Hearing research 235, 23-38.
Srinivasan, A.G., Landsberger, D.M., Shannon, R.V. 2010. Current focusing sharpens local peaks of excitation in cochlear implant stimulation. Hearing research 270, 89-100.
Wells, J., Kao, C., Jansen, Ed., Konrad, P., Mahadevan-Jansen, A. 2005a. Application of infrared light for in vivo neural stimulation. J Biomed Opt 10, 064003.
Wells, J., Konrad, P., Kao, C., Jansen, E.D., Mahadevan-Jansen, A. 2007. Pulsed laser versus electrical energy for peripheral nerve stimulation. Journal of neuroscience methods 163, 326-37.
Wells, J.D., Kao, C., Konrad, P., Mahadevan-Jansen, A., Jansen, E.D. 2006. Biophysical mechanism responsible for pulsed low-level laser excitation of neural tissue. SPIE 6084, 60840X1-7.
Wells, J.D., Kao, C., Mariappan, K., Albea, J., Jansen, E.D., Konrad, P., Mahadevan-Jansen, A. 2005. Optical stimulation of neural tissue in vivo. Optics Letters 30, 504-506.
The National Institute of Health, Cochlear Implants. http://www.nidcd.nih.gov/health/hearing/pages/coch.aspx.
International Search Report dated Dec. 19, 2014 for Application No. PCT/US2014/054107.

\* cited by examiner

SYSTEM AND METHOD FOR ANIMAL-HUMAN NEURAL INTERFACE

CROSS-REFERENCE TO RELATED PATENT APPLICATION

This application claims the benefit, pursuant to 35 U.S.C. §119(e), of U.S. provisional patent application Ser. No. 61/873,720, filed Sep. 4, 2013, entitled "AN ANIMAL-HUMAN NEURAL INTERFACE," by Claus-Peter Richter et al., which is incorporated herein by reference in its entirety.

Some references, which may include patents, patent applications and various publications, are cited in a reference list and discussed in the description of this invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [13] represents the 13th reference cited in the reference list, namely, Richter, C. P., Matic, A. I., Wells, J. D., Jansen, E. D., Walsh, J. T., Jr. 2011. Neural stimulation with optical radiation. Laser Photon Rev 5, 68-80.

STATEMENT AS TO RIGHTS UNDER FEDERALLY-SPONSORED RESEARCH

This invention was made with government support under R01DC011855 awarded by the National Institutes of Health. The government has certain rights in the invention.

FIELD OF THE INVENTION

The invention relates generally to the neural stimulation, and more particularly to system and method for transmitting neural data extracted from an electrical signal of a non-human mammal to a human for animal-human neural interface.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Among neural prostheses, cochlear implants (CI) are considered the most successful devices. To date, they restore some hearing in about 324,200 severe-to-profound deaf individuals by stimulating segments along the length of the tonotopically organized cochlear spiral ganglion[25]. The average cochlear implant user can understand running speech under quiet listening conditions. The scores in standard speech recognition tests for many of the patients are more than 50% and can reach close to 100%. However, the performance suffers in noisy listening environments and for music perception. There is a need in the art for improved neural prostheses that provide improved sensory experiences for patients with impaired hearing.

Auditory stimuli are processed through a complex set of intricate anatomical structures and cellular processes that convert the acoustical stimuli into electrical signals that are then processed into sensory perceptions. The challenges in designing neural prostheses are best understood with a detailed description of the structures and processes involved in, the transmission of auditory stimuli to the brain.

Sound waves travel along the outer ear canal and vibrate the tympanic membrane, which separates the outer ear canal from the middle ear. Vibrations of the tympanic membrane are transmitted through the middle ear to the cochlea by a chain of three ossicles (malleus, incus and stapes). The middle ear compensates some of the impedance-mismatch that exists between the air and the fluid filled space of the cochlea. The stapes inserts into the oval window, an opening at the basal turn of the cochlea. Vibrations of the stapes result in pressure changes in the fluid filled space of the inner ear. A second window in the cochlea, the round window, allows displacing fluids caused by the pressure changes, and vibrations of cochlear soft tissue structures resulted.

Tissue properties, such a stiffness of the soft tissue, change along the cochlea being stiffer at the cochlear base and increasingly compliant towards the cochlear apex. Thus, frequency and level of an acoustic stimulus determine amplitude of the soft tissue vibration and the location site of the vibration along the cochlea. High frequency acoustic stimuli vibrate the basal section of the cochlea while low frequency stimuli vibrate the cochlear apex. The cochlea acts a frequency analyzer, not only for simple pure tone stimuli but also for complex acoustical signals such as speech.

Soft tissue structures, such as the organ of Corti contain the hair cells (outer and inner hair cells) that are able to convert the mechanical vibrations of the soft tissue structures into changes of the cell's membrane potential by bending their hair like extensions, the stereocilia. Amplification of the sound induced vibrations occurs from the outer hair cells, which change their length upon stimulation and the detection of the vibration and subsequent transmitter release by the inner hair cells.

In severe-to-profound deaf, most of the hair cells have been lost and the acoustical signals cannot be transmitted to the remaining auditory nerve. Part of the hearing can be restored by electrically stimulating remaining auditory nerve fibers using a cochlear implant. In other words, the cochlear implant must substitute for this complex set of interactions and directly stimulate the auditory neurons, effectively mimicking the tonotopic arrangement. Commercially available implants stimulate the neurons electrically.

The cochlear implant comprises an electrode array that is implanted in the cochlea with contacts placed at different locations along the path from the oval window to the cochlear apex. The design of speech processors for cochlear implants relies on several assumptions regarding users' perceptual responses to electrical stimulation. These assumptions are that each electrode contact is distinct, both spatially and temporally, or equivalently that electrode interaction (i.e., overlap in fields of stimulation) does not occur. In a successful multichannel cochlear implant, stimulation at one electrode should not affect the perceptual response to stimulation resulting from neighboring electrodes.

Harmonic structure is a common feature for complex sounds, such as those produced by the human voice and musical instrument. Psychoacoustic studies show that the normal auditory system makes good use of harmonic information to perceive pitch, identify instrument timbre, and focus on a target speaker in complex listening situations. As important as it is, how to represent harmonic information in cochlear implants remains topic for research. The key difficulty lies in the inherent coarse spectral and temporal resolution of cochlear implants The restoration of melody perception is one key remaining challenge in cochlear implants. A novel sound coding strategy is proposed that converts an input audio signal into time-varying electrically stimulating pulse trains. A sound is first split into several frequency sub-bands with a fixed filter bank or a dynamic filter bank tracking harmonics in sounds. Each sub-band signal is coherently downward shifted to a low-frequency base band. These resulting coherent envelope signals have Hermitian symmetric frequency spectrums and are thus real-valued. A peak detector or high-rate sampler of half-wave rectified coherent envelope signals in each sub-band further converts the coherent envelopes into rate-varying, interleaved pulse trains. Acoustic simulations of cochlear implants using this new technique with normal hearing listeners, showed significant improvement in melody recognition over the most common conventional stimulation approach used in cochlear implants.

Nonetheless, there remains a bottleneck for the coding for the following reasons: (1) 120 dB in acoustical level difference are compressed to a 6-12 dB change in the current level of the cochlear implant device; (2) more than 50 perceptual channels in a normal hearing subject are reduced to about 4 channels in a cochlear implant patient; and (3) the normal auditory system is characterized by its nonlinearity based on the cochlear mechanics (providing the large dynamic range of 120 dB), its sensitivity, and its frequency selectivity.

Therefore, a heretofore unaddressed need exists in the art to address the aforementioned deficiencies and inadequacies.

SUMMARY OF THE INVENTION

It would be ideal to rebuild the cochlea and use it at the input to a cochlear implant that acts as a frequency analyzer, and level decoder. The objectives of the invention are, among other things, to provide system and method that utilize the pristine cochlea of an animal for the decoding and spike generation. The analysis of the acoustical signal and the extraction of relevant information are done by the healthy inner ear of the animal.

According to the invention, the system uses the normal sensory system of an animal to process and encode the sensory information, records the neural correlates from a chronically implanted electrode in the midbrain of the animal, and transmits the information to a receiver. The animal thus becomes the neural interface for the human, which is superior in coding to any man-made algorithm for encoding sensory information. In certain embodiments, the receiver is implanted in a human and feeds the information to the relevant human nerves. In a preferred embodiment, the sensory information comprises auditory stimuli, the electrode is implanted along the auditory pathway of the service animal, including the nerve cochlear nucleus or the inferior colliculus, and the receiver is implanted in the cochlea of the human.

In one aspect of the invention, the system for transmitting neural data extracted from an electrical signal of a non-human mammal to a human for animal-human neural interface includes an electrode implantable into the animal auditory nerve, brainstem, or midbrain of the non-human mammal, configured to record the electrical signal of the non-human mammal, wherein the electrical signal is in the form of sequences of pulses or pulse trains encoding frequency information of the non-human mammal; a processing device electrically coupled with the electrode, configured to process the electrical signal and convert the processed electrical signal into a digital signal; a transmitting device electrically coupled with the processing device, configured to transmit the digital signal; and a receiving device electrically coupled with the transmitting device, configured to receive the transmitted digital signal, convert the received digital signal into a sensory output perceptible to the human, and apply the sensory output to the human.

In one embodiment, the electrode, the processing device and the transmitting device are operably implanted in, and/or associated with, the non-human mammal, and the receiving device is operably implanted in, and/or associated with the human.

In one embodiment, the transmitting device is integrable into the processing device.

In one embodiment, the electrical signal comprises action potentials generated by the non-human mammal responsive to sensory stimuli.

In one embodiment, the electrode comprises an electrode array with multiple electrode contacts. In one embodiment, the electrode comprises at least 16 contacts.

In one embodiment, the processing device comprises a filter for filtering the recorded electrical signal with a bandpass; an amplifier and level shifter for level shifting and amplifying the filtered electrical signal; and an analog-to-digital (A/D) converter for converting the level shifted and amplified electrical signals to the digital signal. In one embodiment, the bandpass of the filter is in a range of about 0.1-5 kHz, preferably, about 0.3-3 kHz.

In one embodiment, the transmitting device and the receiving device are electrically coupled to each other via a wired or cable connection, or a wireless connection.

In one embodiment, the transmitting device is a broadband wireless transmitting device. In one embodiment, the wireless transmitting device is a Bluetooth wireless transmitter.

In one embodiment, the receiving device comprises a computer, a tablet, a smartphone, or a stereophonic receiver.

In another embodiment, the receiving device comprises a cochlear implant implantable into the human.

In one embodiment, the cochlear implant comprises a cochlear implant electrode array having multiple channels, wherein each channel is operably corresponding to an electrical source used to stimulate neurons of the human. In one embodiment, the number of independent electrical sources used to stimulate the neurons of the human matches with the number of channels recorded by the electrode implanted in the non-human mammal.

In one embodiment, the sensory output comprises pulse signals that map the frequency information of the non-human mammal onto the channels of the cochlear implant implanted in the human.

In one embodiment, the cochlear implant further comprises current sources configured to convert spike times in the recorded electrical signal of the non-human mammal to biphasic electrical pulses that are transmitted to the cochlear implant electrode array to evoke neural responses in the human, wherein the electrical pulses are level adjusted prior to the transmission to the cochlear implant electrode array to ensure that the electrical pulses are substantially at threshold levels so that the input of the electrical pulses to the human is at a base loudness.

In one embodiment, the receiving device further comprises a receiver electrically coupled to the cochlear implant. In one embodiment, the receiver is a wireless receiver.

In one embodiment, the system may further include a controller electrically coupled to the A/D converter, the Bluetooth device and the cochlear implant.

In another aspect, the invention relates to a method for transmitting neural data extracted from an electrical signal of a non-human mammal to a human for animal-human neural interface. In one embodiment, the method includes the steps of exposing the non-human mammal to sensory stimuli; recording the electrical signal of the non-human mammal responsive to the sensory stimuli, wherein the electrical signal is in the form of sequences of pulses or pulse trains encoding frequency information of the non-human mammal; processing the recorded electrical signal and converting the processed electrical signal into a digital signal; transmitting the digital signal; and receiving and converting the digital signal into a sensory output perceptible to the human, and applying the sensory output to the human.

In one embodiment, the electrical signal comprises action potentials generated by the non-human mammal responsive to the sensory stimuli.

In one embodiment, the recording step is performed with an electrode implanted into the auditory nerve, brainstem, or midbrain of the non-human mammal.

In one embodiment, the electrode comprises an electrode array with multiple electrode contacts.

In one embodiment, the step of processing the recorded electrical signal and converting the processed electrical signal into the digital signal comprises the steps of filtering the recorded electrical signal by a filter having a bandpass; level shifting and amplifying the filtered electrical signal by an amplifier and level shifter; and converting the electrical signal to a digital signal by an analog to digital (A/D) converter. In one embodiment, the bandpass of the filter is in a range of about 0.1-5 kHz, preferably, about 0.3-3 kHz.

In one embodiment, the transmitting step is performed with a wired or cable communication protocol, or a wireless communication protocol.

In one embodiment, the step of receiving and converting the digital signal into the sensory output perceptible to the human, and applying the sensory output to the human is performed with a cochlear implant implanted into the human.

In one embodiment, the cochlear implant comprises a cochlear implant electrode array having multiple channels, wherein each channel is operably corresponding to an electrical source used to stimulate neurons of the human.

In one embodiment, the number of independent electrical sources used to stimulate the neurons of the human matches with the number of channels recorded by the electrode implanted in the non-human mammal.

In one embodiment, the sensory output comprises pulse signals that map the frequency information of the non-human mammal onto the channels of the cochlear implant implanted in the human.

In one embodiment, the step of converting the digital signal into the sensory output perceptible to the human, and applying the sensory output to the human comprises the steps of converting spike times in the recorded electrical signal of the non-human mammal to biphasic electrical pulses; and transmitting the converted electrical pulses to the cochlear implant electrode array to evoke neural responses in the human.

In one embodiment, prior to the transmitting step, the step of converting the digital signal into the sensory output perceptible to the human, and applying the sensory output to the human comprises the step of level adjusting the electrical pulses to ensure that the electrical pulses are substantially at threshold levels so that the input of the electrical pulses to the human is at a base loudness.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 3 shows schematically a flow chart of the operation of a system for animal-human neural interface according to another embodiment of the invention. The first element is a recording electrode that is placed in the auditory nerve, brainstem or midbrain of a mammal. The second element processes the recorded analog signal through a band pass filter. The signal is then processed through an adjustable amplifier and is impedance matched. From this step there are two routes that can be taken: (1) the analog signal is digitized by an A/D converter and transmitted to a computer for storage and/or analysis, thereafter, the signal may be transmitted to the cochlear implant; and (2) the second pathway takes the analog signal and discriminates the thresholds for each channel, which determines the spike times in the signal. The threshold discrimination is user controlled based on the optimal threshold level. This operation acts as an analog to digital conversion by taking the continuous signal and converting it to a vector containing zeros and ones.

DETAILED DESCRIPTION OF THE INVENTION

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the phrase "at least one of A, B, and C" should be construed to mean a logical (A or B or C), using a non-exclusive logical OR. It should be understood that one or more operations within a method is executed in different order (or concurrently) without altering the principles of the invention.

As used herein, the term "action potentials" refer to the electric response of nerve fibers or muscle tissues to its stimulation such as electrical stimuli, optical stimuli, and/or acoustic click stimuli. The action potentials are considered as the traveling signals of nerves and the localized changes that contract muscle cells responsive to the stimulation. Compound action potentials are the summation of individual action potentials from single neurons.

As used herein, the term "nerve fiber" refers to a portion of the neuron, namely the axon, which carries action potentials from one end of the neuron to the other. The cochlear nerve fibers originate from neurons of the spiral ganglion and project peripherally to cochlear hair cells and centrally to the cochlear nuclei (cochlear nucleus) of the brain stem. They mediate the sense of hearing.

As used herein, the term "spiral ganglion" refers to the sensory ganglion of the cochlear nerve. The cells of the spiral ganglion send fibers peripherally to the cochlear hair cells and centrally to the cochlear nuclei (cochlear nucleus) of the brain stem.

The term "cochlea," as used herein, refers to a spiral-shaped cavity of the inner ear that resembles a snail shell and contains nerve endings essential for hearing. The cochlea includes three fluid-filled chambers: scala tympani and scala vestibuli (both of which contain perilymph), and scala media (which contains endolymph). The scala tympani and the scala vestibuli are contiguous with each other, merging at the tip of the snail shell, the helicotrema. The stapes transmits vibrations to the fenestra ovalis (oval window) on the outside of the cochlea, which vibrates the perilymph in the scala vestibuli. This in turn vibrates the endolymph in the scala media, thus causing movements of the hair bundles of the hair cells, which are acoustic sensor cells that convert vibration into electrical potentials. The term "hair cells", as used herein, refers to the sensory cells of the auditory system in all vertebrates. In mammals, the hair cells are located within the cochlea's organ of Corti. They derive their name from the tufts of stereocilia that protrude from the apical surface of the cell, a structure known as the hair bundle. Mammalian hair cells come in two anatomically and functionally distinct types: the outer and inner hair cells. Damage to these hair cells results in decreased hearing sensitivity, i.e. sensorineural hearing loss.

The term "cochlear implant", as used herein, refers to a device that is placed into the cochlea to provide sound perception for deaf individuals.

Embodiments of the invention are illustrated in detail hereinafter with reference to accompanying drawings in FIGS. 1-5. It should be understood that specific embodiments described herein are merely intended to explain the invention, but not intended to limit the invention. In accordance with the purposes of this invention, as embodied and broadly described herein, this invention, in certain aspects, relates to system and method for transmitting neural data extracted from an electrical signal of a non-human mammal to a human for animal-human neural interface.

Figure 1:
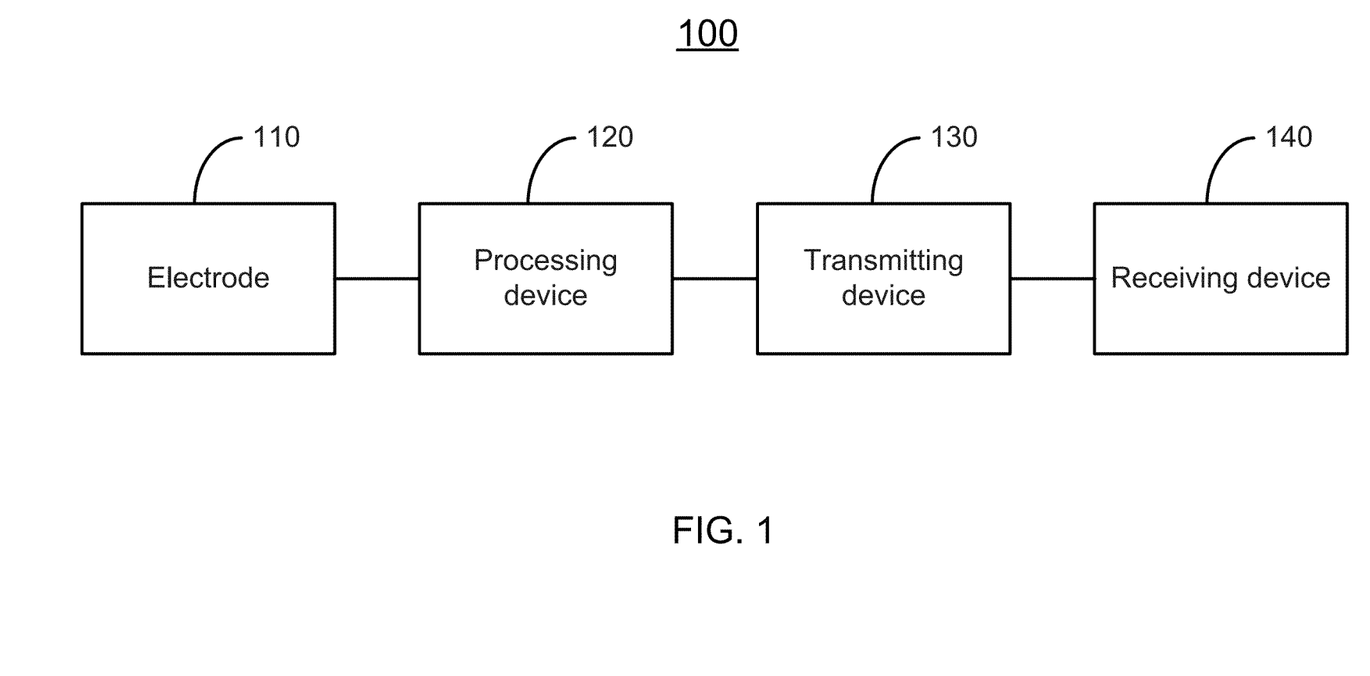
FIG. 1 shows schematically a system for animal-human neural interface according to one embodiment of the invention

Referring to FIG. 1, a system 100 for transmitting neural data extracted from an electrical signal of a non-human mammal to a human is shown according to one embodiment of the invention. Mammals suitable for use with the invention include, but are not limited to, felines, canines and large rodents. Preferred mammals are canines and felines. In the exemplary embodiment, the system 100 includes an electrode 110, a processing device 120, a transmitting device 130 and a receiving device 140. In certain embodiments, the electrode 110, the processing device 120 and the transmitting device 130 are operably implanted in, and/or associated with, the non-human mammal, and the receiving device 140 is operably implanted in, and/or associated with the human. In one embodiment, the transmitting device 130 may be integrable into the processing device 120.

The electrode 110 is implantable into the animal auditory nerve, brainstem, or midbrain of the non-human mammal and is configured to record the electrical signal of the non-human mammal, where the electrical signal comprises action potentials generated by the non-human mammal responsive to sensory stimuli and is in the form of sequences of pulses or pulse trains encoding frequency information of the non-human mammal. In one embodiment, the electrode 110 comprises an electrode array with multiple electrode contacts. In one embodiment, the electrode 110 comprises at least 16 contacts.

The processing device 120 is electrically coupled with the electrode and configured to process the electrical signal and convert the processed electrical signal into a digital signal. In one embodiment, the processing device 120 comprises a filter for filtering the recorded electrical signal with a bandpass; an amplifier and level shifter for level shifting and amplifying the filtered electrical signal; and an analog-to-digital (A/D) converter for converting the level shifted and amplified electrical signals to the digital signal. In one embodiment, the bandpass of the filter is in a range of about 0.1-5 kHz, preferably, about 0.3-3 kHz.

The transmitting device 130 is electrically coupled with the processing device and configured to transmit the digital signal.

The receiving device 140 is electrically coupled with the transmitting device and configured to receive the transmitted digital signal, convert the received digital signal into a sensory output perceptible to the human, and apply the sensory output to the human. In one embodiment, the sensory output comprises pulse signals that map the frequency information of the non-human mammal onto the channels of the cochlear implant implanted in the human.

In one embodiment, the transmitting device 130 and the receiving device 140 are electrically coupled to each other via a wired or cable connection, or a wireless connection.

In one embodiment, the transmitting device 130 is a wireless transmitting device. In one embodiment, the wireless transmitting device is but not limited to a Bluetooth wireless transmitter. It will be appreciated by those skilled in the art that a transmitting device operated in the other types of communication protocols can also be utilized to practice the invention.

In one embodiment, the receiving device 140 comprises a computer, a tablet, a smartphone, or a stereophonic receiver.

In another embodiment, the receiving device 140 comprises a cochlear implant implantable into the human.

In one embodiment, the cochlear implant comprises a cochlear implant electrode array having multiple channels, where each channel is operably corresponding to an electrical source used to stimulate neurons of the human. In one embodiment, the number of independent electrical sources used to stimulate the neurons of the human matches with the number of channels recorded by the electrode implanted in the non-human mammal.

In one embodiment, the cochlear implant further comprises current sources configured to convert spike times in the recorded electrical signal of the non-human mammal to biphasic electrical pulses that are transmitted to the cochlear implant electrode array to evoke neural responses in the human, where the electrical pulses are level adjusted prior to the transmission to the cochlear implant electrode array to ensure that the electrical pulses are substantially at threshold levels so that the input of the electrical pulses to the human is at a base loudness.

In one embodiment, the receiving device 140 further comprises a receiver electrically couple to the cochlear implant. In one embodiment, the receiver is a wireless receiver.

In one embodiment, the system may further include a controller electrically coupled to the A/D converter, the Bluetooth device and the cochlear implant.

In another aspect of the invention, the system includes some or all of six elements: a first element for recording action potentials from a non-human mammal, a second element for processing the action potentials and converting the action potentials into digital signals, a third element for transmitting the digital signals, a fourth element for receiving the digital signals, a fifth element for converting those signals into pulse signals, and a sixth element for applying those pulse signals to a human to be perceptible by the human. The first, second and third elements are implanted in, and/or associated with, a non-human mammal, while the fourth, fifth and sixth elements are implanted in, and/or associated with a human.

Figure 2A:
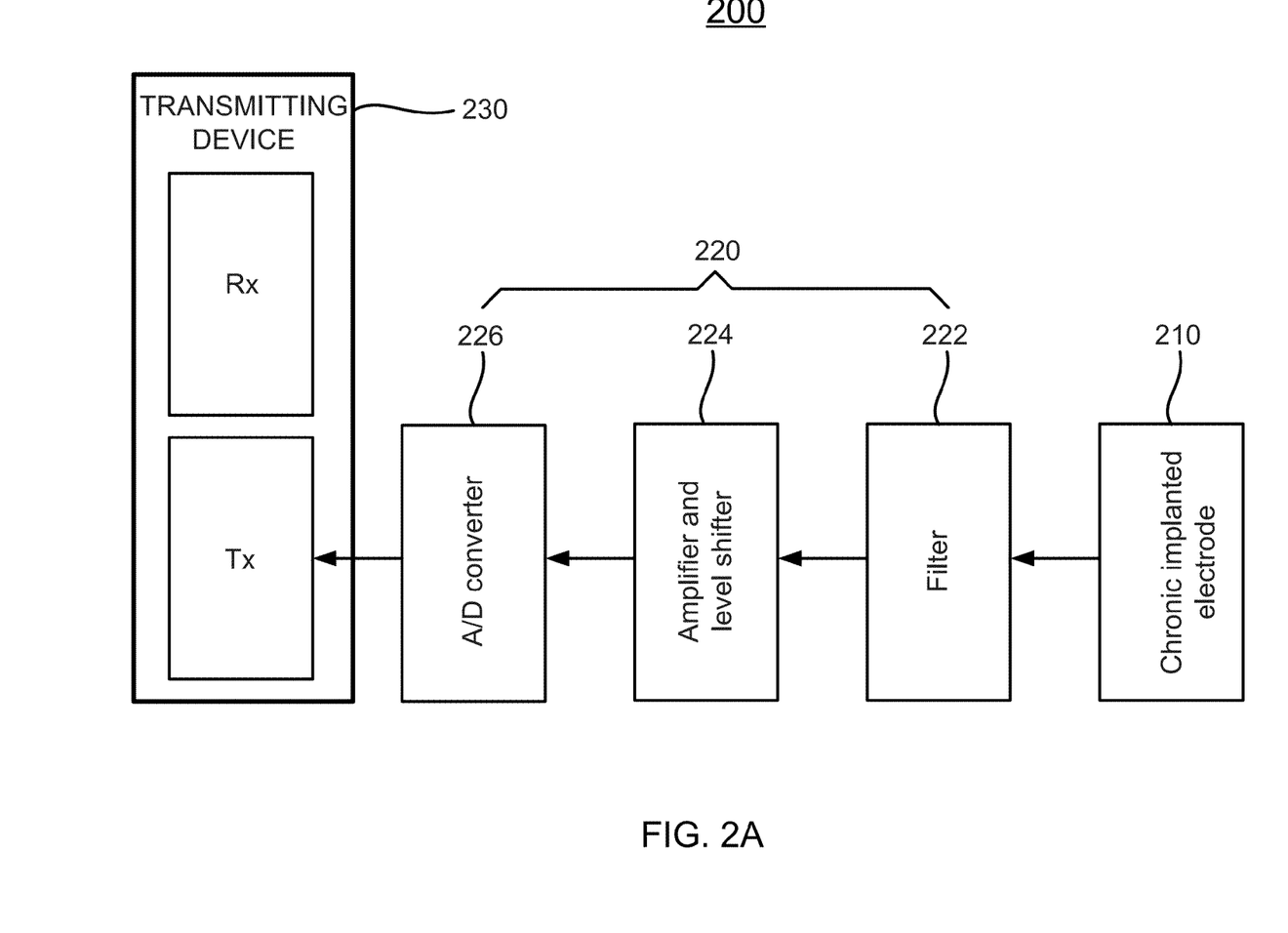
FIG. 2A shows schematically a functional block diagram representing the elements implanted in, and/or associated with, a non-human mammal, of a system for animal-human neural interface according to one embodiment of the invention, where the elements are adapted for recordings of action potentials by an electrode implanted in the non-human mammal; processing the action potentials and converting the action potentials into a digital signal, and transmitting the digital signal, where Tx presents a data transmitter and Rx represents a data receiver.
Figure 2B:
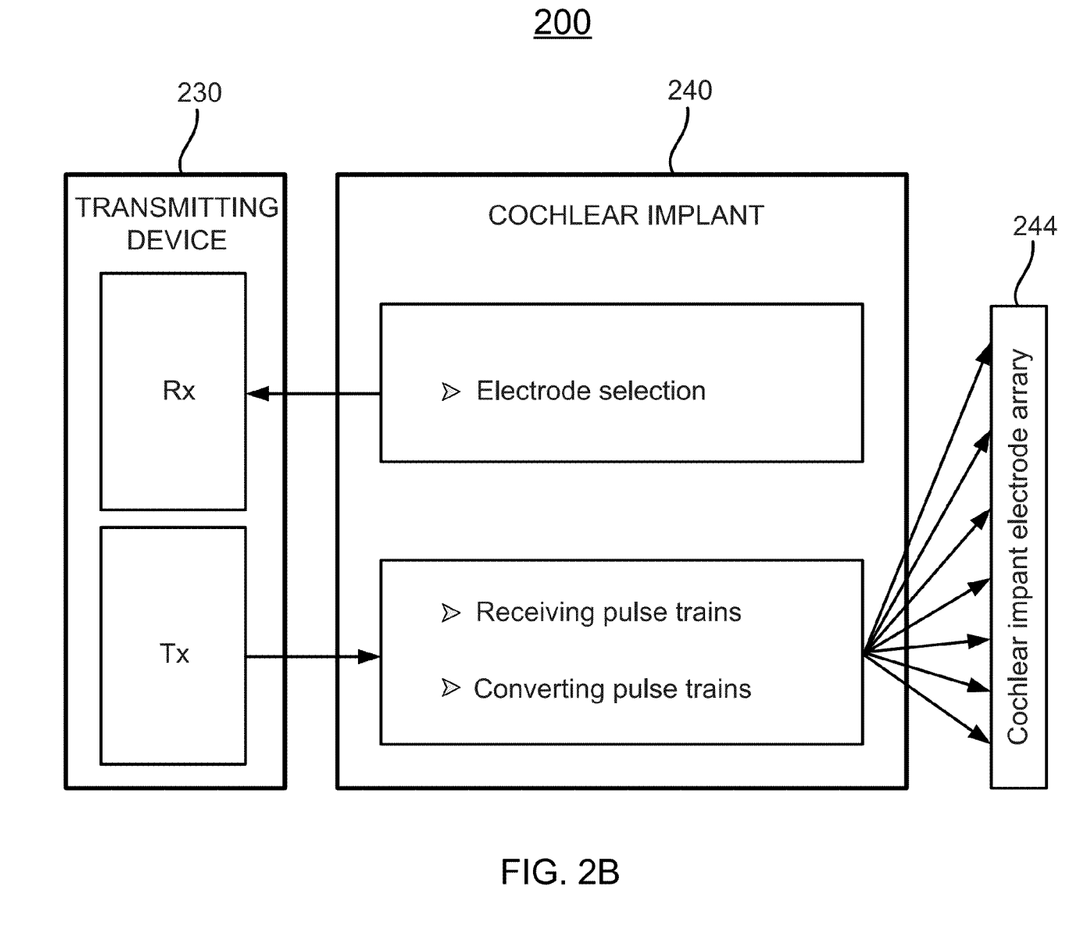
FIG. 2B shows schematically a functional block diagram representing the elements implanted in, and/or associated with, a human, of a system for animal-human neural interface according to one embodiment of the invention, where the elements are adapted for receiving the digital signal; converting the digital signal into a sensory output perceptible to the human, and apply the sensory output to the human.

Referring to FIGS. 2A and 2B, in one embodiment, the first element of the system 200 includes a chronic implanted electrode 210 that is first implanted in the auditory nerve, brainstem or midbrain of a non-human mammal. Mammals suitable for use with the invention include, but are not limited to, felines, canines and large rodents. Preferred mammals are canines and felines. The chronic implanted electrode 210 may be any one of several commercially available electrodes designed for recording pulse trains encoding sensory frequencies including, but not limited to, electrodes from NeuroNexus Technologies. Alternatively, the chronic implanted electrode 210 may be designed and built de novo. The chronic implanted electrode 210 is preferably an electrode array with multiple electrode contacts. In certain embodiments, the electrode 210 comprises at least 16 contacts, preferably, between 16 and 100 contacts. It will be appreciated by those skilled in the art that the placement of the electrode array within the midbrain of the animal can be validated by methods available in the literature [7, 12, 15, 16, 19]. Other preferred features of the electrode include low resistance, biocompatibility, long-term stability. In certain embodiments, for the purpose of recording auditory pulse trains, the electrode is implanted in the inferior colliculus.

Once the electrode 210 has been implanted, it is connected to the second element of the system 200, which is a processing device 220 that converts the recorded action potentials from the non-human animal into digital signals. In one embodiment shown in FIG. 2A, the processing device 220 comprises a filter 222, and amplifier and level shifter 224, and an A/D converter 226. In one embodiment, the processing device 220 is adapted from the device described by Sharma et al. [14]. The device described by Sharma is built to process information received from an electrical stimulation device and to provide feedback to a user for purposes of controlling the electrical stimulation device; thus, the device of Sharma has features that may not be useful for the invention.

In one embodiment, the third element of the system 200 may include a transmitting device 230, which may optionally be integrated into the processing device 220. In one embodiment, the transmitting device 230 may be operated in a wired or cable communication protocol, or a wireless communication protocol. In one embodiment, the transmitting device 230 is a wireless transmitter. In one embodiment, the wireless transmitting device 230 is a Bluetooth wireless transmitter. It will be appreciated by those skilled in the art that a transmitting device operated in the other types of communication protocols can also be utilized to practice the invention.

In one embodiment, the processing device 220 has dimensions suitable for strapping the processing device to the body of the mammal bearing the electrode component of the system. Considerations in the preferred placement of the processing device 220 include, but are not limited to, the size and dimension of the processing device, the size and physical structure of the mammal, and proximity to the connection to the electrode component.

Once the electrode 210 is implanted in the mammal and connected to the processing device 220, the mammal is exposed to the sensory stimuli. The information encoded by the midbrain of the mammal in trains of action potentials (pulses) is recorded by the electrode 210. The analog signal is then amplified and converted into a digital signal that is transmitted to the receiving device 240 of the system 200.

In the exemplary embodiment shown in FIG. 2B, the receiving device including a cochlear implant 240 integrates the fourth, fifth and sixth elements of the system, which receive the digital signal, convert the digital signal into pulse signals perceptible by the human, and apply the pulse signals to the human, respectively.

The receiving device of the system can be any device capable of communicating with the transmitting device and producing a sensory output perceptible to a human. In one embodiment, the receiving device is a desktop computer, a laptop computer, a tablet, a smartphone or a stereophonic receiver. In another embodiment, the receiving device is an implant. In one embodiment, the implant is a cochlear implant. In one embodiment, the communication of the receiving device with the transmitting device occurs via a wired or cable connection. In one embodiment, the communication is via a wireless connection. In one embodiment, the communication occurs via a Bluetooth connection.

In the exemplary embodiment shown in FIGS. 2A and 2B, the system 200 comprises an electrode array 210 capable of recording pulse trains encoding auditory frequencies, a processing device 220 comprising a filter 222, an amplifier and level shifter 224, and an A/D converter 226, a wireless transmitting device 230 optionally integrated into the processing device 220, and a cochlear implant 240 comprising a wireless signal receiver. Once the receiving device in the cochlear implant 240 has received the information from the transmitting device 220, the cochlear implant 240 then converts the sequence of pulses into current pulses and delivers them at tonotopically corresponding electrode contacts 244 along the cochlea. In other words, the frequency map of the animal is mapped onto the human cochlear implant electrode 244 in the human subject. Tonotopically adequate information is sent to the nerve of the cochlear implant user. A schematic block diagram depicting a preferred embodiment of the invention from the receiving device to the cochlear implant is shown in FIG. 2B.

In order to optimize the delivery of the tonotopically adequate information to the cochlear implant user, the number of independent electrical sources used to stimulate the neurons should match the number of channels recorded by the implanted electrodes in the mammal. Currently, the only commercially available cochlear implant with at least 16 truly independent sources is the Advanced Bionics implant with 16 such independent sources. It will be appreciated by those skilled in the art that implants with other number of independent sources can also be utilized to practice the invention.

In certain embodiments, it may be desirable to modify cochlear implants to overcome these limitations. For example, several engineering approaches can be used to establish the tonotopic stimulation of the cochlea. The most feasible approach today is stimulation with an array of light sources that can be placed along the cochlea. In a particular embodiment, the light sources such as vertical cavity surface emitting electrodes (VCSELs), micro light emitting diodes (µLEDs) or light guides are placed along the tonotopically organized spiral ganglion as described in U.S. Pat. No. 7,833, 257, which is hereby incorporated by reference in its entirety.

In certain embodiments, the neural responses that are recorded with the multichannel electrode (16 or more channels) implanted in the non-human mammal are typically not more 500 µV. Frequency analysis of previously recorded signals showed that the maximum of the magnitude plots are at about 1 kHz. Therefore, to improve the signal to noise ratio, the recordings are filtered with a bandbass filter before being amplified by 60 dB. Level shifters are needed to convert the bipolar signals into positive-only signals, which are then digitized using analog-to-digital converters. Data are typically digitized at 12 bit and 27,000 samples/second, but may be digitized at other sampling rates. The beginning of the neural signal recording is triggered by a free running internal clock or is determined by the user/cochlear implant.

Bidirectional telemetry allows both automatic or user control neural signal recording and the sequential transmission of the data from the stimulating electrodes. The Bluetooth microchip supports the standard Bluetooth protocol Version 2.0+ EDR, capable of 3 Mb/s data transmission rate. In a similar device presented by Sharma et al. [14] a rate to 0.5 Mb/s was used, which was adequate for continuous transmission of 16-bit neural data.

Figure 3:
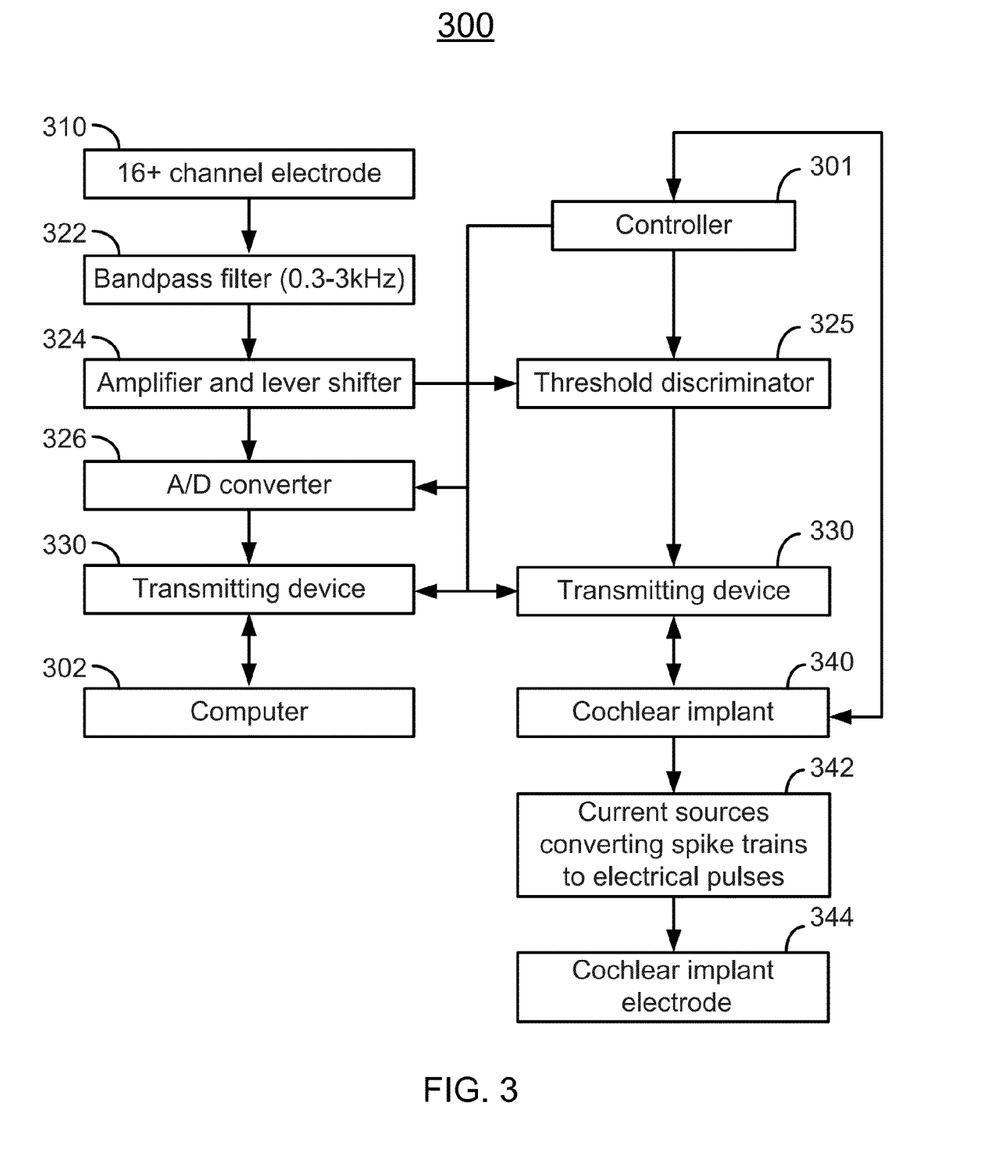

FIG. 3 shows schematically a flow chart of the operation of the system 300 of a specific preferred embodiment of the invention. At first, a recording electrode 310 with at least 16 channels and an impedance of approximately 1-10 kHz is placed (or implanted) in the auditory nerve, brainstem, or midbrain of a mammal. Once it is implanted, the recording electrode 310 can record the electrical signal, such as action potentials, of the non-human mammal. The action potentials may be generated by the non-human mammal, for example, responsive to sensory stimuli. In certain embodiments, the recorded electrical signal is an analog signal in the form of sequences of pulses or pulse trains of the action potentials. The recorded analog signal is processed through a band pass filter 322 with a range of frequency from about 0.3 to 3 kHz. The filtered signal is then processed through an adjustable amplifier and level shifter 324 and is impedance matched. From this step there are two routes that can be taken.

Route 1: the processed analog signal is digitized by an A/D converter 326 and transmitted by a transmitting device 330, for example, through a wireless connection, to a computer 302 for storage and/or analysis. Thereafter, the digitized signal can be transmitted to the cochlear implant 340 by the transmitting device 330. In one embodiment, the transmitting device 330 is a wireless transmitter. In one embodiment, the wireless transmitting device 330 is a Bluetooth wireless transmitter. It will be appreciated by those skilled in the art that a transmitting device operated in the other types of communication protocols can also be utilized to practice the invention. In certain embodiments, the chip for the analog to digital conversion and the chip for the Bluetooth transmission must be controlled to allow the conversion of the signal between the two, as described by Sharma et al. [14].

Route 2: the thresholds of the processed analog signal are discriminated by a threshold discriminator 325 for each channel, which determines the spike times in the signal. The threshold discrimination is user controlled based on the optimal threshold level. This operation acts as an analog to digital conversion by taking the continuous signal and converting it to a vector containing zeros and ones. The ones correspond to a neural spike, encoding the spike time information in the vector. The threshold discrimination is user controlled to allow for optimized speech processing. The spike times are then sent via the Bluetooth device 330 to the cochlear implant 340 implanted in the human user. These spike times are then converted by the current sources 342 of the cochlear implant user to biphasic electrical pulses that are sent to the cochlear implant electrode 344 to evoke neural responses in the cochlear implant user. The electrical pulses must be level adjusted prior to transmission to the cochlear implant electrode 344 to ensure that the signal is just at threshold level so the input to the user is at base loudness.

In certain embodiments, the analog-to-digital conversion and handshake between the A/D converter 326 and the Bluetooth device 330 are controlled via an internal clock, for example, of a controller 301. The controller 301 may include one or more processors. In addition, the controller 301 is also coupled with the cochlear implant 340 for controlling the operation thereof.

Figure 4:
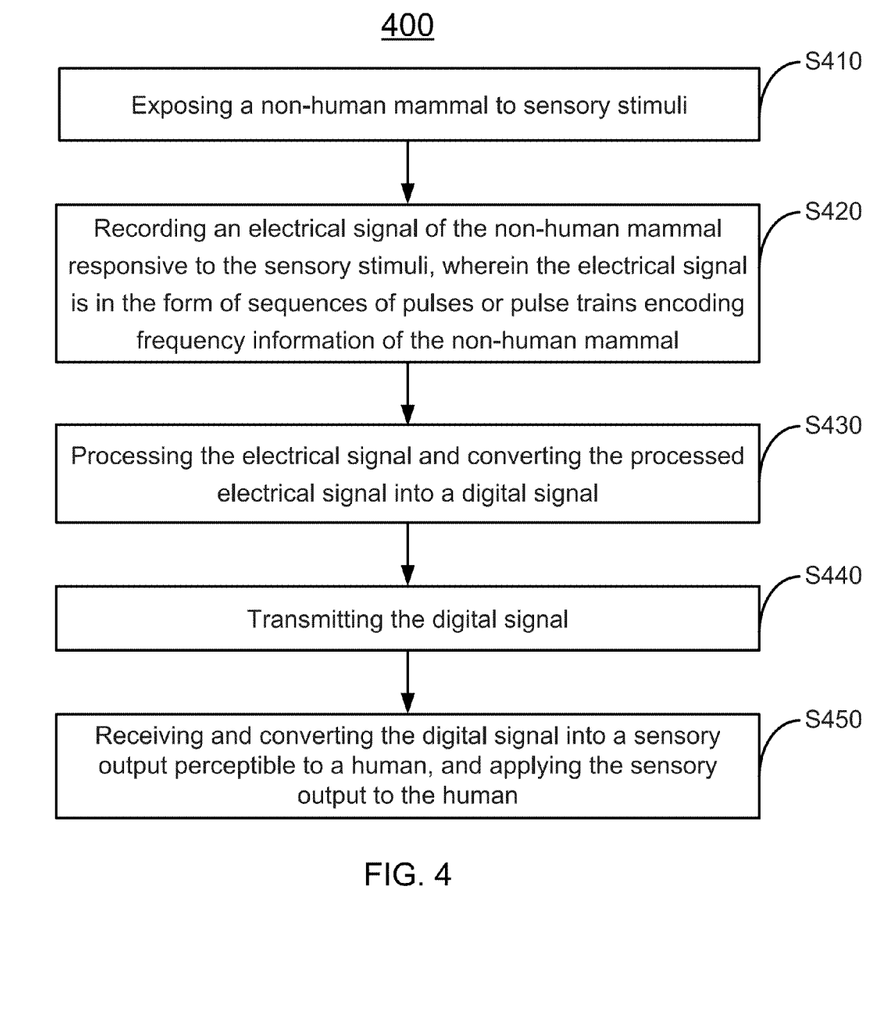
FIG. 4 shows schematically a flow chart of a method for transmitting neural data extracted from an electrical signal of a non-human mammal to a human for animal-human neural interface according to one embodiment of the invention.

Referring to FIG. 4, a flow chart of a method 400 of animal-human neural interface for transmitting neural data extracted from an electrical signal of a non-human mammal to a human is shown according to one embodiment of the invention. In the exemplary embodiment, the method 400 includes the following steps.

At step S410, the non-human mammal exposed to sensory stimuli. Prior to the step S410, an electrode with multiple electrode contacts is implanted into the animal auditory nerve, brainstem, or midbrain of the non-human mammal. In one embodiment, the electrode has at least 16 contacts.

At step S420, the electrical signal of the non-human mammal responsive to the sensory stimuli is recorded by the implanted electrode. The electrical signal comprises action potentials generated by the non-human mammal responsive to sensory stimuli and is in the form of sequences of pulses or pulse trains encoding frequency information of the non-human mammal.

At step S430, the recorded electrical signal is processed and converted into a digital signal. In certain embodiments, the recorded electrical signal needs to be filtered by a filter having a bandpass in a range of about 0.1-5 kHz, preferably, about 0.3-3 kHz; the filtered electrical signal is level shifted and amplified by an amplifier and level shifter; and the electrical signal is then converted to a digital signal by an A/D converter.

At step S440, the digital signal is transmitted to a receiver. In one embodiment, the transmitting step is performed with a wired or cable communication protocol, or a wireless communication protocol.

At step S450, the digital signal is received and converted into a sensory output perceptible to the human, and the sensory output is then applied to the human. In certain embodiments, the step S450 is performed with a cochlear implant implanted into the human. The details of the cochlear implant is disclosed above, and not repeated herein.

In certain embodiments, the step S450 comprises the steps of converting spike times in the recorded electrical signal of the non-human mammal to biphasic electrical pulses; and transmitting the converted electrical pulses to the cochlear implant electrode array to evoke neural responses in the human.

In certain embodiments, prior to the transmitting step, the step S450 further comprises the step of level adjusting the electrical pulses to ensure that the electrical pulses are substantially at threshold levels so that the input of the electrical pulses to the human is at a base loudness.

According to the embodiments of the invention, a desirably additional feature is added to cochlear implant devices, which bypasses the conventional coding strategies and uses directly the information transmitted from the wireless transmitting device to the wireless receiving device. In contemporary implants, algorithms of the speech processor separate the acoustical speech signal into a number of frequency bands extract level information within this band and convert the information in a sequence of electrical pulses. In the current invention, the recorded signals from the animals are converted directly into trains of electrical pulses, which are delivered to corresponding sites along the cochlea of the human cochlear implant user. The stimulation sites are matched with the best frequencies of the units recorded in the animal. Sound processing features of the implant could be bypassed. In a preferred embodiment, the patient (cochlear implant user) decides the coding strategy, provided by the speech processor, or the sequence recorded in the animal.

The benefits of the system and method of the invention are multifold and overcome limitations of conventional cochlear implants:

1. The acoustical dynamic range of 120 dB is mapped physiologically into the train of action potentials recorded by the electrode. Thus the full dynamic range and the "acoustical contrast" can be fully used.

2. The frequency selectivity is existent and the frequency for each of the contacts is mapped exactly to a normal functioning ear.

3. Since the neural responses are of stochastic nature, no cross correlation exist between the trains. The human cochlear implant thus can take the lowest current levels to stimulate the nerve, which increases the populations of nerve fibers stimulated independently at a time and will increase the spatial selectivity. As a consequence, all 16 to 22 contacts of existing cochlear implant electrodes can be used to stimulate in parallel. The increase in number of independent channels is estimated to be at least a factor of 5.

4. Maximum stimulation rates are well below 200 Hz, the maximum repetition rate obtained from neural recordings of isolated neural units [9-11].

5. Because the stimulation occurs at a threshold level and the pulse repetition rate is below 200 Hz, the power consumption of the cochlear implant is decreased significantly, compared to the conventional cochlear implants where the pulse repetition rate is typically about 1 kHz.

These and other aspects of the invention are further described in the following section. Without intend to limit the scope of the invention, further exemplary implementations of the same according to the embodiments of the invention are given below.

Example 1

Placing an Electrode Array in the Midbrain of a Non-Human Mammal

A silicon-substrate, thin-film multichannel penetrating electrode array (A1×16-5 mm-100-177, NeuroNexus Technologies, Ann Arbor, Mich.) is stereotactically placed in the ICC. Each array has 16 recording sites (about 177 $\mu m^2$/site) along a single shank at center-to-center intervals of 100 $\mu m$. To access the ICC, the right temporalis muscle is reflected, and an approximate 5×5 mm opening is made in the right parietal bone just dorsal to the parietal/temporal suture and just rostral to the tentorium. A small incision in the dura mater is made and the multichannel electrode array is advanced through the occipital cortex into the ICC using a 3D-micromanipulator (Stoelting, Kiel, Wis.). The latter is attached to the stereotactic head holder.

The electrode array is inserted into the ICC on a dorsolateral to ventromedial trajectory at approximately 45 off the parasagittal plane in the coronal plane. Using this trajectory, the electrode array passes through the central nucleus of the ICC approximately orthogonal to its isofrequency laminae [18, 19]. After the initial placement of the distal tip of the electrode into the ICC, the electrode is advanced while an acoustic tone pip is presented. Proper placement of the electrode is determined when neural responses from the distal contact of the array can be stimulated with a tone pip between 16 and 25 kHz.

After placing the electrode array, the exposed skull and dura mater are covered and protected from dehydration with gauze sponges (Dukal Corporation, Hauppauge, N.Y.) soaked with Ringer's lactate solution.

Example 2

Data Acquisition from the Electrode Implanted in a Non-Human Mammal

Compound action potentials are recorded. The round window electrode is connected to a differential amplifier (ISO-80, WPI, Sarasota, Fla.) with a high input-impedance (greater than $10^{12}\Omega$) and a gain of about 60 dB. The responses are bandpass filtered (0.33 kHz) using the differential amplifier.

Example 3

Transmitter Associated with a Non-Human Mammal

The device described by Sharma et al. [14] has been rebuilt, removing the component responsible for electrical stimulation. It is a multifunctional programmable controller with unidirectional data telemetry, implemented using existing commercial microchips and a standard Bluetooth protocol, which adds convenience, reliability, and ease-of-use to neuroprosthetic devices. A controller, weighing about 190 g, is placed on the animal's back and provides a sustained telemetry rate of about 500 kb/s. In certain embodiments, the transmitter can be redesigned to be fully implantable.

As described by Sharma et al. [14], in the continuously-active state, the controller consumes about 420 mW and operates without recharge for about 8 hrs. It features independent 16-channel data acquisition. It is possible to record evoked neuronal responses. Flexibility, scalability, cost-efficiency, and user-friendly computer written codes in MATLAB allows the use of animal testing for variety of applications.

Example 4

Perception by a Human of Neural Data Recorded from a Non-Human Mammal

In this exemplary embodiment, neural data have been recorded from the inferior colliculus in the guinea pig while playing a sentence from the speech-in-noise-test (SIN) to the animal's ear. The recordings are the same as obtained for pure tone stimuli of stimulation with the laser as described in [8, 12, 13]. The recorded trains of action potentials were then processed and played through a loudspeaker and were presented to a normal hearing listener who could see at the same time the lips of a second human forming the same sentence with the lips but not vocalizing. The normal listener could decode the sentence. Performance increased with increase in number of channels presented at the same time.

The results demonstrate that the system of the invention delivers sensory information perceptible to a human.

Example 5

Results From Initial Experiments

Figure 5:
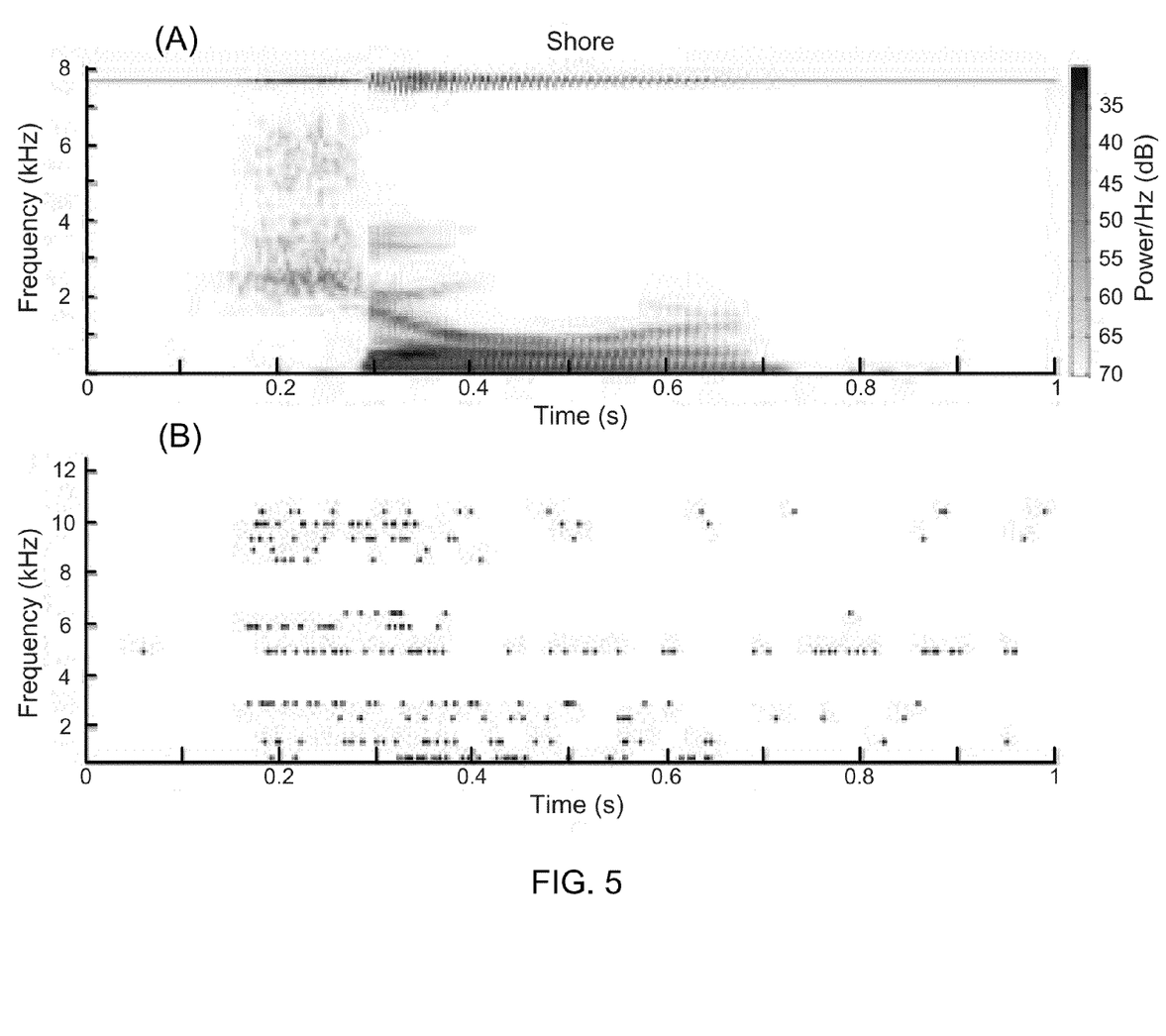
FIG. 5 shows (A) the spectrogram of the word "shore", where the y-axis represents the frequencies and the x-axis the times of the acoustical signal, and the color is a measure for the magnitude; darker values are larger, brighter color such as yellow and white show low magnitudes; and (B) corresponding sequences of action potentials that were recorded in the guinea pig inferior colliculus, while the word was played to the animal's ear. The frequency on the left side provides the pure tone best frequency of each unit.

For the exemplary experiments, 53 words from the commercially available SIN test were played to the ear of an anesthetized guinea pig, while neural activity of an identified and stable unit in the central nucleus of the inferior colliculus were recorded. The best frequency of the unit to pure tone acoustical stimulation was determined as well. After the conclusion of the experiments, a spectrogram of the acoustical signal was produced, as shown in FIG. 5(A). It can be seen that for the word "shore", shown in the example, some of the information is represented at high frequencies (greater than 2 kHz), but most of the frequency information is found at frequencies below 2 kHz. FIG. 5(B) shows the corresponding neural responses, which were recorded from the inferior colliculus. Each dot in a horizontally dotted line represents an action potential and each horizontally dotted line represents a different unit. The location of the line along the y-axis is determined by the unit's best frequency to the pure tone stimulation.

The pulse sequences of each line, shown in FIG. 4(B), are played to the cochlear implant user. Hereby, the natural frequency map of the cochlear implant user could not be reproduced because of the current lack of the animal data. What is presented is a distorted map towards high frequencies, missing all the low frequency information. During the test sessions, the subjects were asked to describe the lexical content and the hearing experience to the words.

Both cochlear implant users could identify a rhythm and loudness change of the sequence although the current amplitude was not changed. Parallel stimulation at neighboring electrodes was possible. Subject 1 (S1) described the words as drops falling into water, or a boat cruising through the water. For some words, S1 described pitch changes and two beats. Subject 2 (S2) was more detailed in the description of the hearing experience. Regarding beats and rhythm, S2 reported similar experiences like S1. In addition to S1, S2 volunteered the information that the speaker is a male (which is correct). S2 was not asked for this information. Moreover, S2 put lexical content to the words. The lexical content did not match the true content, but was robust. In other words, S2 could clearly identify words out of sequences of words, which were presented in a random order.

In the detailed analysis of the experiments, it was realized that important acoustical information below 2 kHz was not presented to the cochlear implant user. At present, there were only two neural recordings from neurons at best frequencies below 2 kHz. To determine how such a distorted acoustical signal sounds when played to a normal hearing subject, the acoustical content of the words to the frequency range was limited, which were available to the cochlear implant user during testing. Since low frequency information was largely missing, the words became very distorted and the acoustical contend resembled very well the description of the hearing experience of the two cochlear implant users.

In brief, the invention, among other things, discloses a novel approach that uses the normal sensory system of an animal to process and encode the sensory information, records the neural correlates from a chronically implanted electrode in the midbrain of the animal, and transmits the information to a receiver. The animal thus becomes the neural interface for the human, which is superior in coding to any man-made algorithm for encoding sensory information.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

LIST OF REFERENCES

[1]. Berenstein, C. K., Mens, L. H., Mulder, J. J., Vanpoucke, F. J. 2008. Current steering and current focusing in cochlear implants: comparison of monopolar, tripolar, and virtual channel electrode configurations. Ear and hearing 29, 250-60.

[2]. Choi, C. T., Hsu, C. H. 2009. Conditions for generating virtual channels in cochlear prosthesis systems. Annals of biomedical engineering 37, 614-24.

[3]. Koch, D. B., Downing, M., Osberger, M. J., Litvak, L. 2007. Using current steering to increase spectral resolution in CII and HiRes 90K users. Ear and hearing 28, 38S-41S.

[4]. Landsberger, D. M., Srinivasan, A. G. 2009. Virtual channel discrimination is improved by current focusing in cochlear implant recipients. Hearing research 254, 34-41.

[5]. Mens, L. H., Berenstein, C. K. 2005. Speech perception with mono- and quadrupolar electrode configurations: a crossover study. Otol Neurotol 26, 957-64.

[6]. Middlebrooks, J. C., Bierer, J. A. 2002. Auditory cortical images of cochlear-implant stimuli: coding of stimulus channel and current level. J Neurophysiol 87, 493-507.

[7]. Middlebrooks, J. C., Snyder, R. L. 2010. Selective electrical stimulation of the auditory nerve activates a pathway specialized for high temporal acuity. J Neurosci 30, 1937-46.

[8]. Moreno, L. E., Rajguru, S. M., Matic, A. I., Yerram, N., Robinson, A. M., Hwang, M., Stock, S., Richter, C.-P. 2011. Infrared neural stimulation: beam path in the guinea pig cochlea. Hearing research PMID: 21763410.

[9]. Ohlemiller, K. K., Echteler, S. M. 1990. Functional correlates of characteristic frequency in single cochlear nerve fibers of the Mongolian gerbil. J Comp Physiol A 167, 329-38.

[10]. Ohlemiller, K. K., Siegel, J. H. 1998. Temporal aspects of the effects of cooling on responses of single auditory nerve fibers. Hearing research 123, 78-86.

[11]. Ohlemiller, K. K., Echteler, S. M., Siegel, J. H. 1991. Factors that influence rate-versus-intensity relations in single cochlear nerve fibers of the gerbil. J Acoust Soc Am 90, 274-87.

[12]. Richter, C.-P., Rajguru, S. M., Matic, A. I., Moreno, E. L., Fishman, A. J., Robinson, A. M., Suh, E., Walsh Jr., J. T. 2011. Spread of cochlear excitation during stimulation with optical radiation: Inferior colliculus measurements. Journal of neural engineering 8, 056006.

[13]. Richter, C. P., Matic, A. I., Wells, J. D., Jansen, E. D., Walsh, J. T., Jr. 2011. Neural stimulation with optical radiation. Laser Photon Rev 5, 68-80.

[14]. Sharma, V., McCreery, D. B., Han, M., Pikov, V. 2010. Bidirectional telemetry controller for neuroprosthetic devices. IEEE transactions on neural systems and rehabilitation engineering: a publication of the IEEE Engineering in Medicine and Biology Society 18, 67-74.

[15]. Shepherd, R. K., Baxi, J. H., Hardie, N. A. 1999. Response of inferior colliculus neurons to electrical stimulation of the auditory nerve in neonatally deafened cats. J Neurophysiol 82, 1363-80.

[16]. Shepherd, R. K., Linahan, N., Xu, J., Clark, G. M., Araki, S. 1999. Chronic electrical stimulation of the auditory nerve using non-charge-balanced stimuli. Acta otolaryngologica 119, 674-84.

[17]. Snyder, R. L., Bierer, J. A., Middlebrooks, J. C. 2004. Topographic spread of inferior colliculus activation in response to acoustic and intracochlear electric stimulation. J Assoc Res Otolaryngol 5, 305-22.

[18]. Snyder, R. L., Bierer, J. A., Middlebrooks, J. C. 2004. Topographic spread of inferior colliculus activation in response to acoustic and intracochlear electric stimulation. J Assoc Res Otolaryngol 5, 305-22.

[19]. Snyder, R. L., Middlebrooks, J. C., Bonham, B. H. 2008. Cochlear implant electrode configuration effects on activation threshold and tonotopic selectivity. Hearing research 235, 23-38.
[20]. Srinivasan, A. G., Landsberger, D. M., Shannon, R. V. 2010. Current focusing sharpens local peaks of excitation in cochlear implant stimulation. Hearing research 270, 89-100.
[21]. Wells, J., Kao, C., Jansen, E. D., Konrad, P., Mahadevan-Jansen, A. 2005a. Application of infrared light for in vivo neural stimulation. J Biomed Opt 10, 064003.
[22]. Wells, J., Konrad, P., Kao, C., Jansen, E. D., Mahadevan-Jansen, A. 2007. Pulsed laser versus electrical energy for peripheral nerve stimulation. Journal of neuroscience methods 163, 326-37.
[23]. Wells, J. D., Kao, C., Konrad, P., Mahadevan-Jansen, A., Jansen, E. D. 2006. Biophysical mechanism responsible for pulsed low-level laser excitation of neural tissue. SPIE 6084, 60840X1-7.
[24]. Wells, J. D., Kao, C., Mariappan, K., Albea, J., Jansen, E. D., Konrad, P., Mahadevan-Jansen, A. 2005. Optical stimulation of neural tissue in vivo. Optics Letters 30, 504-506.
[25]. The National Institute of Health, Cochlear Implants. http://www.nidcd.nih.gov/health/hearing/pages/coch.aspx.

What is claimed is:

1. A method for transmitting neural data extracted from an electrical signal of a non-human mammal to a human, comprising:
    exposing the non-human mammal to sensory stimuli;
    recording the electrical signal of the non-human mammal responsive to the sensory stimuli, wherein the electrical signal is in the form of sequences of pulses or pulse trains encoding frequency information of the non-human mammal;
    processing the recorded electrical signal and converting the processed electrical signal into a digital signal;
    transmitting the digital signal; and
    receiving and converting the digital signal into a sensory output perceptible to the human, and applying the sensory output to the human,
    wherein the step of receiving and converting the digital signal into the sensory output perceptible to the human, and applying the sensory output to the human is performed with a cochlear implant implanted into the human.

2. The method of claim 1, wherein the electrical signal comprises action potentials generated by the non-human mammal responsive to the sensory stimuli.

3. The method of claim 1, wherein the recording step is performed with an electrode implanted into the auditory nerve, brainstem, or midbrain of the non-human mammal.

4. The method of claim 3, wherein the electrode comprises an electrode array with multiple electrode contacts.

5. The method of claim 1, wherein the step of processing the recorded electrical signal and converting the processed electrical signal into the digital signal comprises:
    filtering the recorded electrical signal by a filter having a bandpass;
    level shifting and amplifying the filtered electrical signal by an amplifier and level shifter; and
    converting the electrical signal to a digital signal by an analog to digital (A/D) converter.

6. The method of claim 5, wherein the bandpass of the filter is in a range of about 0.1-5 kHz, preferably, about 0.3-3 kHz.

7. The method of claim 1, wherein the transmitting step is performed with a wired or cable communication protocol, or a wireless communication protocol.

8. The method of claim 1, wherein the cochlear implant comprises a cochlear implant electrode array having multiple channels, wherein each channel is operably corresponding to an electrical source used to stimulate neurons of the human.

9. The method of claim 8, wherein the number of independent electrical sources used to stimulate the neurons of the human matches with the number of channels recorded by the electrode implanted in the non-human mammal.

10. The method of claim 9, wherein the sensory output comprises pulse signals that map the frequency information of the non-human mammal onto the channels of the cochlear implant implanted in the human.

11. The method of claim 1, wherein the step of converting the digital signal into the sensory output perceptible to the human, and applying the sensory output to the human comprises:
    converting spike times in the recorded electrical signal of the non-human mammal to biphasic electrical pulses; and
    transmitting the converted electrical pulses to the cochlear implant electrode array to evoke neural responses in the human.

12. The method of claim 11, wherein, prior to the transmitting step, the step of converting the digital signal into the sensory output perceptible to the human, and applying the sensory output to the human comprises:
    level adjusting the electrical pulses to ensure that the electrical pulses are substantially at threshold levels so that the input of the electrical pulses to the human is at a base loudness.

13. A method of using a non-human mammal as a neural interface for a human, comprising:
    transmitting neural data extracted from an electrical signal of the non-human mammal; and
    receiving and converting the neural data into a sensory output perceptible to the human, and applying the sensory output to the human,
    wherein the neural data is a digital data; and
    wherein the step of receiving and converting the digital signal into the sensory output perceptible to the human, and applying the sensory output to the human is performed with a cochlear implant implanted into the human.

14. The method of claim 13, wherein the step of transmitting the neural data extracted from the electrical signal of the non-human mammal, comprising:
    exposing the non-human mammal to sensory stimuli;
    recording the electrical signal of the non-human mammal responsive to the sensory stimuli;
    processing the recorded electrical signal and converting the processed electrical signal into the digital signal; and
    transmitting the digital signal.

15. The method of claim 14, wherein the electrical signal is in the form of sequences of pulses or pulse trains encoding frequency information of the non-human mammal.

16. The method of claim 15, wherein the electrical signal comprises action potentials generated by the non-human mammal responsive to the sensory stimuli.

17. The method of claim 14, wherein the recording step is performed with an electrode implanted into the auditory nerve, brainstem, or midbrain of the non-human mammal.

18. The method of claim 17, wherein the electrode comprises an electrode array with multiple electrode contacts.

19. The method of claim 13, wherein the transmitting step is performed with a wired or cable communication protocol, or a wireless communication protocol.

20. The method of claim 13, wherein the cochlear implant comprises a cochlear implant electrode array having multiple channels, wherein each channel is operably corresponding to an electrical source used to stimulate neurons of the human.

* * * * *